United States Patent [19]

Hanson

[11] Patent Number: 5,344,315

[45] Date of Patent: Sep. 6, 1994

[54] MULTI-STRAND ORTHODONTIC ARCH WIRES AND METHODS FOR USE THEREOF

[75] Inventor: G. Herbert Hanson, Hamilton, Canada

[73] Assignee: Hamilton Ortho Inc., Hamilton, Canada

[21] Appl. No.: 160,124

[22] Filed: Dec. 2, 1993

[51] Int. Cl.$^5$ .............................................. A61C 3/00
[52] U.S. Cl. ........................................ 433/20; 433/24
[58] Field of Search ............................. 433/18, 20, 24

[56] References Cited

U.S. PATENT DOCUMENTS

| | | | |
|---|---|---|---|
| 5,018,969 | 5/1991 | Andreiko et al. | 433/20 |
| 5,046,948 | 9/1991 | Miura | 433/20 |
| 5,080,584 | 1/1992 | Karabin | 433/20 |

OTHER PUBLICATIONS

*Journal of Clinical Orthodontics*, Feb. 1991, vol. XXV, No. 2 pp. 84–86, 90, 92, 93 and 95.

*Primary Examiner*—Cary E. O'Connor
*Attorney, Agent, or Firm*—Rogers & Scott

[57] ABSTRACT

A new multi-strand orthodontic arch wire comprises a plurality of wire strands of superelastic shape recovery metal alloy wrapped helically parallel to one another along the length of the wire, the ratio of the longitudinal pitch P of the wire to the external diameter D of the wire being between six and twelve. Such a wire is able to slide more freely in the bracket slots, and is less likely to breakage, than the short pitch wires previously used. A wire with a hollow central core, can also operate as a compression spring by frictionally engaging it with adjacent orthodontic elements, such as brackets, and arranging that its strands are spread radially apart from a neutral configuration, or it can operate as a traction spring by arranging that its strands are closed radially inward from a neutral configuration, the spring action being produced by the urge of the strands to return to the neutral configuration. Cored wires can act as a compression spring, but not as a traction spring. Partial cores strands can be provided to localize the spring action to specific parts of the wire. The wires can be provided with crimpable end members. The shape recovery metal alloy can be any one of nickel/titanium; nickel/titanium/copper; copper/zinc/aluminum; copper/zinc/aluminum/manganese; copper/aluminum/nickel; and copper/aluminum/nickel/manganese.

17 Claims, 5 Drawing Sheets

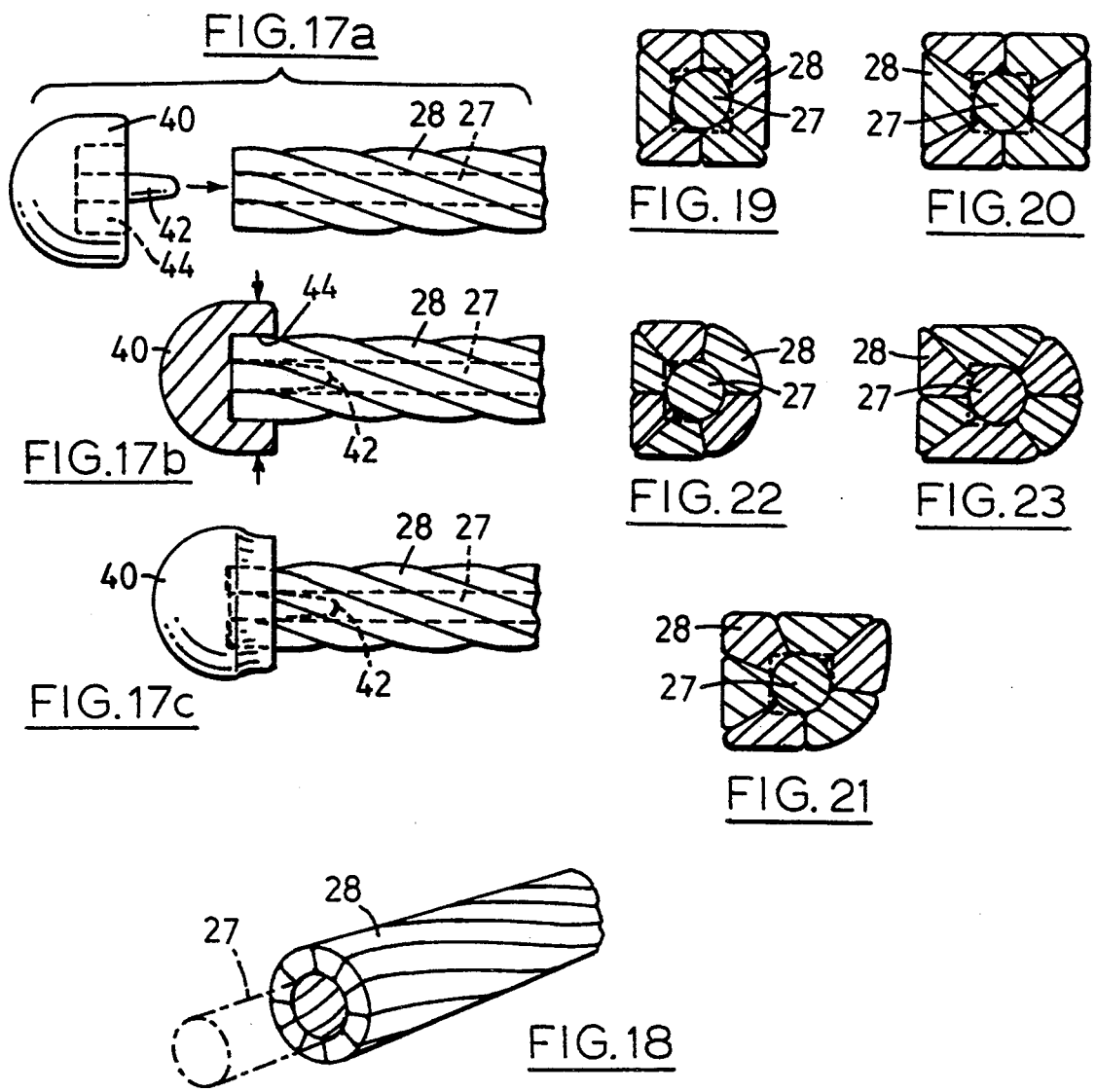
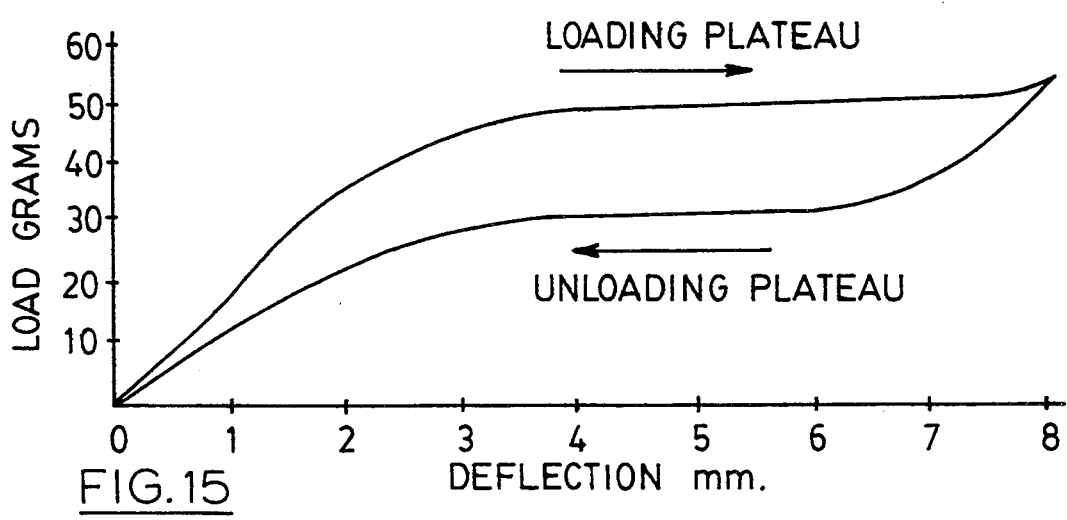

MULTI-STRAND ORTHODONTIC ARCH WIRES AND METHODS FOR USE THEREOF

FIELD OF THE INVENTION

This invention is concerned with improvements in multi-strand orthodontic arch wires that are used in orthodontic procedures to connect together a plurality of brackets attached to the teeth, the wires being operative to move the brackets, thereby moving the teeth to a desired conformation set by the arch wire. The invention is also concerned with new methods for the use of such arch wires in orthodontic procedures.

REVIEW OF THE PRIOR ART

The majority of orthodontic procedures employ a plurality of brackets that are attached to respective teeth, usually by cementing them to the teeth, together with one or more arch wires, so called because they are preformed to an optimum arch shape corresponding to the desired conformation of the teeth at the conclusion of the procedure. The wire is engaged in a cooperating mesial-distal extending slot in each of the brackets, the wire usually being bent from its arch shape to permit this, but not so far that it will take a permanent set, so that it can return under its inherent resilience to its original shape. The wire is attached to each bracket by a ligating wire, or by a ligating elastomeric loop, or by a self-ligating spring that is part of the bracket. An example of a bracket employing a self-ligating spring is that disclosed and claimed in my U.S. Pat. Nos. 4,248,588 and 4,492,573.

Typically the arch-wire receiving slot is rectangular in cross section in the gingival occlusal plane, and the first arch wire used is an "undersize" multistrand very springy wire of circular transverse cross section, and of very low load deflection rate. Such a wire is a very loose fit in the bracket slots, so that the correcting forces it can apply via the brackets to the teeth are correspondingly small, as is desired to avoid the possibility of tissue damage and/or root resorbtion. If additional sliding movements of the brackets along the wire are needed to produce corrective retraction or protraction tooth movements, these are usually produced by compression or extension springs mounted on or parallel to the wire so as to be operative between a pair of cooperating brackets, or between a bracket and an appliance attached to the wire, such as a stop, a hook, or a buccal tube.

After several weeks the corrective effect of this undersize wire decreases to an inefficient value, and it is replaced with a less springy wire of larger diameter; this successive replacement is continued until the wire in use is of the largest diameter that can be inserted in the slot while not producing excessive sliding friction between the wire and the bracket that would inhibit the desired sliding movements. This arch wire of largest diameter may still be of inherently springy material, and can then be replaced by wires of progressively increasing stiffness; the diameter and the inherent stiffness may be increased together. At some stage the round cross section wires are usually replaced by rectangular cross section wires which fit snugly within the rectangular cross section slots to give greater control of tipping (commonly called "torquing") of the teeth about the mesial distal slot axis.

It is a fundamental objective with orthodontic procedures that they proceed as rapidly as possible, consistent with the avoidance of the above described undesired side effects. Orthodontic procedures are only possible because the teeth are securely anchored in the bone of the jaw to the extent that they withstand without movement the surprisingly high impact forces to which they are subjected in normal operation, and yet they can be moved in that bone while remaining securely attached by the persistent application of relatively extremely small forces. This desired movement in the bone takes place by means of a relatively complex process involving special cells which absorb bone at the positive pressure site (Osteoclasts), and which deposit bone (Osteoblasts) at the opposite negative pressure site, the process requiring a minimum or threshold amount of force for it to become established. The tissue and bone of the jaw have a generous blood supply and this should be maintained at as normal a level as possible to maintain the cells healthy and active and thus facilitate this cellular action; an adequate blood supply is also needed to maintain the surrounding supporting tissue in healthy condition.

There is therefore a specific predeterminable range of force that should be employed, namely sufficient to ensure the cellular action takes place, while not so large that the blood supply is reduced, and it is found that in practice the force required is comparatively relatively low. It is difficult in practice to give numerical values to these forces, since the application will vary from tooth to tooth in the same mouth, but it is known that they are considerably smaller than those which are encountered in conventional edgewise procedures. High forces do not therefore necessarily result in faster movement of the teeth, and can instead result in even slower movement because of the resultant restriction of the blood supply and consequent inhibition of the entire process; there is also as described above the increased possibility of damage to or even death of the tissue and the teeth roots and permanent resorption of the bone of the jaw. The optimum procedures are therefore those in which light moving couples within a narrow range above the threshold value are applied as persistently as possible and, as indicated above, such procedures are readily established with the arch wires of the invention.

Multi-strand wires have an inherent advantage over solid wires in that they can be made to have a much lower load deflection rate than a solid wire of the same material and dimensions, and a large number of such wires of different types and characteristics are already commercially available. They may for convenience in review for the purposes of this application be classified in two major separate groups, namely "wrapped" wires, in which a plurality of wire strands (usually from three to eight) are twisted tightly together along a longitudinal axis to lie alongside each other, and "braided" wires, in which the wire strands repeatedly cross over one another as they extend along the long dimension of the wire. Another two-group classification is that some wires have the strands wrapped or braided around a central core strand, while others have no such separate core strand; the core strand when provided may be of the same diameter as the other strands, or of different diameter, usually slightly larger. A further two-group classification is that some wires have the strands twisted or braided together without further modification of their cross section shape, so that its circumference has a typical repeated connected semicircle profile, while others are formed to a specific cross section shape, such as circular, square or rectangular, so that the circumference is relatively smooth. Most wires are provided with a smooth exterior finish to facilitate the sliding action.

One characteristic that all of these wires have in common is that the wire strands are tightly twisted or braided together with a very short pitch, and typically the pitch of the twist or braid of the individual strands has a value of not more than about four times the diameter (or equivalent diameter for non-circular cross section wires) of the wire. One purpose of such tight twisting or braiding is to ensure that the material is stressed to such a high value that subsequently the strands will not unravel while in the patient's mouth, when the resulting sharp protruding ends could cause damage and irritation to the surrounding soft tissue. Many manufacturers give as a desirable feature of their wire that it will not unravel when a piece is cut from a longer length, and in practice it would be difficult to provide a treatment for the cut ends to prevent unravelling without either changing the desirable mechanical properties of the wire (e.g. if the wire is heated to braze or fuse the ends together), or without making the wire difficult to thread through the brackets and other appliances (e.g. if the ends are cemented together). Orthodontists would in any case prefer to use a wire that can be cut and used without an end sealing step. Another purpose is to ensure that the wire is not deformed from its preset cross section as it is forced into the bracket arch wire slots.

Various so-called shape recovery metal alloys, also frequently called superelastic metal alloys, have been developed which are highly resistant to overstressing and resultant permanent deformation, as compared to the stainless steels commonly used hitherto. Wires made of these alloys can be bent to a desired shape and "set" in that shape by suitable heat treatment; subsequently if heated above a transformation temperature they will return to their original shape. The atomic structure which produces this phenomenon also causes these alloys to exhibit the so-called superelasticity, whereby they provide a relatively constant restoring force over the wide range of deflection that they are able to tolerate. A preferred alloy in industry is nickel/titanium, usually with a nominal atomic composition of 50% nickel and 50% titanium, with small additions of copper, iron, cobalt or chromium, the alloy being subjected to a heat treatment to develop the desired characteristic. One particularly useful alloy comprises 55% nickel and 45% titanium, while another comprises equal amounts of nickel and titanium with 10 atomic % of copper. Other alloys are also known such as copper/zinc/aluminium (usually 15-25 weight % zinc, 6-9 weight % aluminium and the balance copper); copper/zinc/aluminium/manganese; copper/aluminium/nickel (usually 13-14 weight % aluminium, 3-4 weight % nickel and the balance copper); and copper/aluminium/nickel/manganese. At this time the nickel/titanium alloys are preferred in that they have the greatest ductility, more recoverable motion, excellent corrosion resistance comparable to series 300 stainless steels, stable transformation temperatures for shape recovery (memory) effect, high biocompatibility, and the ability to be electrically heated for shape recovery. Their special properties make them particularly suitable for the manufacture of arch wires, and there have been a number of proposals for their use in braided wires, as exemplified by U.S. Pat. Nos. 5,018,969, issued May 28, 1991, and 5,080,584, issued Jan. 14, 1992.

It is the desire of both orthodontists and their patients that the procedures should proceed as rapidly as possible, with the proviso indicated above that the forces employed are not such as to cause damage to the tissue or the teeth. It has been found that the appropriate use of light correcting forces can result in procedures that are at least as fast, and can even be significantly faster, than the prior procedures using heavier forces, while ensuring reduced risk of damage, and there is therefore a corresponding desire to provide arch wires that provide such light forces during as many as possible of the stages of the procedure.

SUMMARY OF THE INVENTION

It is a principal object of the invention therefore to provide a new multi-strand arch wire.

It is another object to provide a new multi-strand arch wire that is also able to function as a compression or extension spring for effecting mesial-distal tooth movements.

It is another principal object to provide a new method of using such an arch wire in orthodontic procedures.

In accordance with the invention there is provided an orthodontic arch wire for use in combination with a plurality of orthodontic elements attached to respective teeth in an orthodontic procedure;
   the arch wire comprising a plurality of wire strands of superelastic shape recovery metal alloy wrapped helically parallel to one another along the length of the wire;
   wherein the ratio P/D of the longitudinal pitch P of the wire to the external diameter D of the wire is between six and twelve.

The wire may be coreless so as to have a hollow cylindrical centre;
   whereby at least a portion of the wire when frictionally engaged with two adjacent orthodontic elements with the strands of the portion spread radially apart from a neutral wrapped configuration acts between those two adjacent orthodontic elements as a compression spring by its urge to return to the neutral wrapped configuration. Alternatively, at least a portion of the wire when frictionally engaged with two adjacent orthodontic elements with the strands of the portion closed radially inward from a neutral wrapped configuration acts between those two adjacent orthodontic elements as a traction spring by its urge to return to the neutral wrapped configuration.

The material of the wire strands may be selected from the group of superelastic shape recovery metal alloys consisting of nickel/titanium; nickel/titanium/copper; copper/zinc/aluminium; copper/zinc/aluminium/manganese; copper/aluminium/nickel; and copper/aluminium/nickel/manganese. Preferably, the material of the wire strands is nickel/titanium alloy of a nominal atomic composition of 50% nickel and 50% titanium, with small additions of copper, iron, cobalt or chromium.

The wire may be provided along a part only of its length with a partial wire strand core, and either the anterior portion of the wire for engagement with brackets on incisor teeth is provided with a partial wire strand core, or the posterior portions of the wire for engagement with brackets on molar teeth are provided with respective partial wire strand cores.

The arch wire may be used in combination with molar end tubes into which its ends protrude, wherein the length of the wire is such that its anterior portion extends labially of the orthodontic brackets into which it is to be inserted so as to permit its functioning also as a compression spring. Such a combination may also comprise stop members on the wire and butting the molar end tubes to limit the protrusion of the wire ends into the tubes.

Alternatively the arch wire may be used in combination with molar end tubes into which its ends protrude;
  at least one of the molar end tubes having a respective anchor hook thereon;
  at least one hook member attached to the wire spaced from the molar end tube having a hook thereon;
  and a ligation member extending between the molar tube hook member and the hook member to apply traction to the wire so as to permit its functioning also as a traction spring.

The arch wires may be used in combination with an end stop member at at least one end thereof, the end stop member having a core member that protrudes into the wire central hollow, and an annular recess into which the wire protrudes to permit the end member to be crimped on the wire end.

The exterior of the wire may be formed to a non-circular cross section.

The exterior of the wire may be formed to a circular cross section, and the strands from which the wire is formed are preformed to be of truncated segmental cross section.

Also in accordance with the invention there is provided a new method of using an orthodontic arch wire in an orthodontic procedure;
  wherein the arch wire comprises a plurality of wire strands of superelastic shape recovery metal alloy wrapped helically parallel to one another along the length of the wire, and the ratio P/D of the longitudinal pitch P of the wire to the external diameter D of the wire is between six and twelve;
  comprising frictionally engaging at least a portion of the wire with two orthodontic members so that the strands of the portion between the two orthodontic members are spread radially apart from a neutral wrapped configuration, whereby the said portion of the wire acts as a compression spring by its urge to return to the neutral wrapped configuration.

Alternatively the new method comprises frictionally engaging the wire portion with the two orthodontic members so that the strands are closed radially inward, whereby the portion of the wire acts as a traction spring by its urge to return to the neutral wrapped configuration.

DESCRIPTION OF THE DRAWINGS

Particular preferred embodiments of the invention will now be described, by way of example, with reference to the accompanying diagrammatic drawings, wherein:

FIG. 15 is a typical desirable stress strain characteristic for a multi-strand wire of the shape recovery superelastic metals used for the invention;

FIGS. 17a, 17b and 17c are side elevations, with FIG. 17b also a partial cross section showing a crimpable end stop for attachment to the end of a wire and the manner in which it fastened to the end of the wire;

FIG. 18 is a perspective view of a coreless arch wire of the invention of circular cross section to illustrate a preferred method of manufacturing such a wire; and FIGS. 19–23 are respective transverse cross sections through non-circular cross section arch wires that are further embodiments of the invention.

DESCRIPTION OF THE PREFERRED EMBODIMENTS

The multi-strand arch wires of the invention are employed in the well known "light-force" technique in which each bracket is attached to a respective tooth in an attitude such that, as the arch wire returns to its original arch shape from the non-arch shape it has assumed upon insertion into the bracket slots, the teeth are moved toward their desired optimized positions and attitudes. To achieve this the torque requirements (rotation about a mesial distal axis), angulation requirements (rotation about a labial lingual axis), and first order pre-adjustments, are obtained by suitable shaping of the bracket bases, particularly of their lingual surfaces and variation of their thicknesses, so that the bracket slots are aligned along the wire when the teeth are in their optimum positions.

Figure 1:
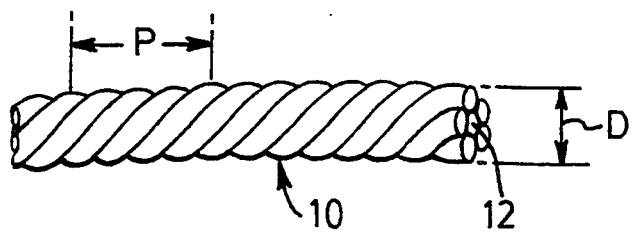
FIG. 1 is a side elevation of a prior art wrapped multi-strand arch wire.

FIG. 1 illustrates a typical wrapped, cored, prior art arch wire 10 comprising five round cross section strands wrapped helically parallel to one another about a central round cross section core strand 12. The pitch of the wire, namely the length along its axis for each strand to complete a full 360 degree helical turn, is indicated by P, while the external diameter of the wire is indicated by D. Other prior art wires that are available commercially comprise from three up to nine wires, and usually they are all of the same diameter. With the particular wire illustrated the value of the ratio P/D is about two, and it is found with such wires that the value is not more than about three or four.

Figure 2:
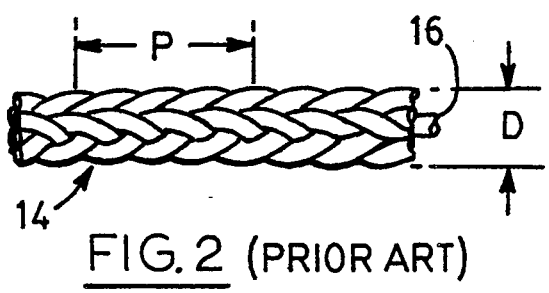
FIG. 2 is a side elevation of a prior art braided multi-strand arch wire.

FIG. 2 illustrates a typical woven or braided, cored, prior art arch wire 14 of pitch P and diameter D comprising six round cross section strands braided helically parallel to one another about a central round cross section core strand 16; the value of the ratio P/D is about two and one half.

Figure 3:
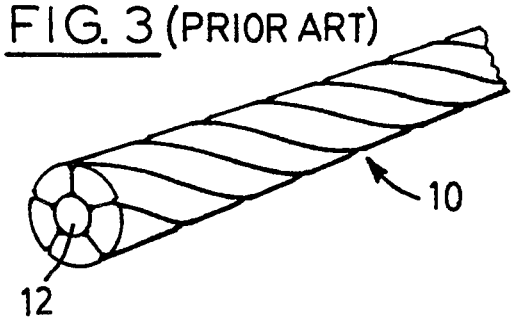
FIG. 3 is a side elevation of a prior art wrapped multi-strand arch wire which has been shaped subsequent to the wrapping step to provide a smooth exterior surface.

FIG. 3 illustrates a wrapped, cored prior art wire that has been formed, usually by a rolling operation, to a more smoothly circular cross section so as minimise sliding friction and the possibility of breakage of the wire, as will be explained below. The additional manufacturing step that this entails does of course increase the cost of production. Formed wrapped or braided wires are also available of other than circular cross section, such as square and rectangular. When the cross section is non-circular the value of P will be the same, but it is necessary to calculate an equivalent diameter D, namely the diameter of a circle having the same transverse cross section area. It is yet again found that with such wires the value of the ratio P/D is in the range of two to four.

Figure 4:
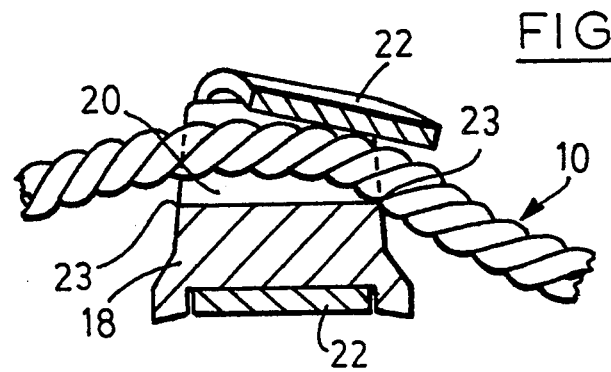
FIG. 4 is a cross section in a mesial distal plane through a bracket at the mesial distal slot, showing a prior art multi-strand wrapped arch wire lodged therein, and illustrating a possible reason for high sliding friction and/or breakage found with such wires.

FIG. 4 illustrates a typical detrimental situation that it is believed arises during the use of a prior art wrapped or braided wire in an orthodontic procedure, this situation at least causing excessive sliding friction between the wire and the bracket, and frequently leading to breakage of the wire during the procedure. Thus, the wire 10 is shown as engaged in the mesial-distal extending slot 20 of a bracket 18, which as illustrated is a self-ligating bracket of the type described and claimed in my U.S. Pat. No. 4,492,573, the disclosure of which is incorporated herein by this reference. Such a bracket comprises a ligating spring member 22 which engages the labial side of the arch wire and urges the wire lingually against the labial facing wall of the slot. The detrimental situation will however also be obtained when using any other form of ligature, such a twisted wire or elastic loop. Owing to the short pitch of the wire the pronounced external grooves between immediately adjacent wires extend at such a steep inclination to the length of the wire that they lie approximately labially-lingually, and there is a high probability that, as illustrated, one of these grooves is entered by one of the two relatively sharp labial-lingual extending edges 23 that are formed at the junctions between the slot labial wall and the bracket body mesial and distal walls. Such engagement is particularly likely when the wire has been highly deflected, as illustrated in FIG. 4, to enable it to be engaged in the bracket slots of adjacent badly displaced teeth, this deflection increasing its inclination considerably. Such edge/groove engagement clearly will prevent any free sliding of the wire through the slot. In use the wire is subjected continuously and repeatedly to a variety of different, strong, varying forces produced by the normal dentition and jaw movements of the patient, particularly chewing movements, and these forces become highly concentrated along the thin line of the engagement. The wire usually is in the patient's mouth for at least several months without respite, and it believed to be most likely that this trapping of the wire against an edge and concentration of the strong forces to which it is continuously subjected, is the most likely cause of the unexpected wire breakages that are and have been encountered in practice, both with the multi-strand stainless steel wires previously used, and with the currently available multi-strand superelastic alloy wires. It was anticipated that the adoption of superelastic alloys for the wires would remove this problem, but this has proven not to be the case.

An indication that this analysis of the problem is correct is the fact that such breakages are substantially reduced to the point of virtual elimination by the adoption of smooth circumference wires, as illustrated by FIG. 3. Such wires are still manufactured with values for the ratio P/D of not more than about three or four and, as explained above, are more expensive to manufacture, without the potential of the other advantages of the wires of the present invention, as will be explained below.

Figure 6:
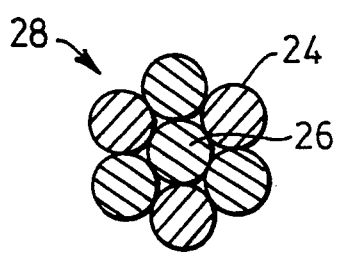
FIG. 6 is a transverse cross section through the wire of FIG. 5, taken on the line 6—6 therein.
Figure 5:
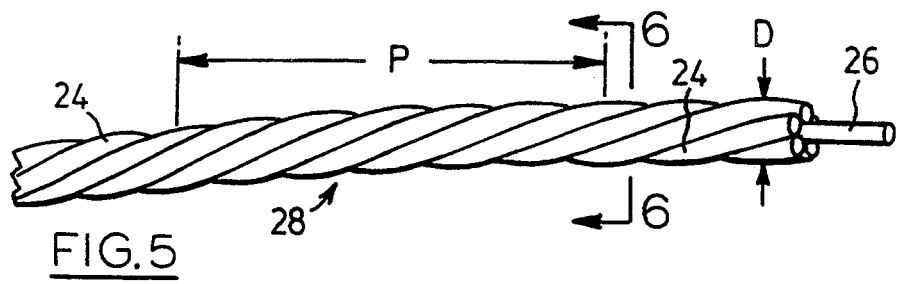
FIG. 5 is a side elevation of a wrapped cored multi-strand arch wire which is a first embodiment of the invention.

FIGS. 5 and 6 are respectively a side elevation and a transverse cross section of an arch wire of the invention, the wire comprising a plurality of wrapping strands 24 (six in this embodiment) of a superelastic metal alloy, such as a nickel/titanium alloy, wrapped helically parallel to one another about a central core strand 26 so as to have a P/D ratio of at least six. The wire takes unexpected advantage of the special property of the relatively enormous elastic range of these alloys that the wire strands can be wound with this much increased P/D ratio and, provided that they subsequently have been heat treated to set them to the required final shape, they will retain this shape without unravelling as pieces are cut from a longer length to form the arch wire. Although the extreme end portions may be unravelled accidentally during certain procedures (e.g. the insertion of the ends into terminal anchoring tubes on the back molars) they seek so strongly to return to their closely wrapped condition that a simple spinning manipulation is sufficient to wrap them closely back around the core strand. This much higher P/D ratio also ensures that, despite the extreme deflections that are permissible with these highly flexible cables without permanent set, the external grooves do not attain an inclination such that they are likely to become engaged with the bracket edges, as with the prior art wires of FIGS. 1 and 2, and cause excessive sliding friction and breakage.

An upper limit is set to the ratio P/D in that if it is too large even strands of superelastic alloy will begin to unravel too easily, and accordingly the ratio should not normally exceed twelve. Preferably, for manufacturing convenience, and to obtain a circumference that is as smooth as possible when the wire is not to be subsequently formed, at least all of the exterior wrapping strands are of the same diameter. The core strand may be of the same or slightly less diameter than the wrapping strands; there is little or no advantage to it being much smaller in diameter, but it can be somewhat larger, especially if a stiffer wire for a subsequent stage of the procedure is desired. The diameters D of the wires used in orthodontic procedures are usually in the range 0.38 mm to 0.56 mm (0.015 in to 0.022 in). In a particular cored arch wire embodiment of the invention for use with a bracket having a slot 20 of 0.55 mm (0.022 in) gingival occlusal dimension, and of 0.525 mm (0.021 in) labial lingual dimension, the value of D is 0.51 mm (0.020 in) with a preferred tolerance of ±0.0125 mm (0.0005 in), so that the value of P is between 3 mm and 6 mm (0.125 in and 0.25 in). The core wire strand can be of diameter from 0.127 mm (0.005 in) to 0.304 mm (0.012 in) with a preferred value of 0.178 mm (0.007 in), this value of course setting the number and diameter of the wrapping strands to obtain the desired final external diameter.

Figure 8:
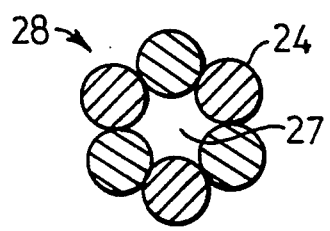
FIG. 8 is a transverse cross section through the wire of FIG. 7, taken on the line 8—8 therein.
Figure 7:
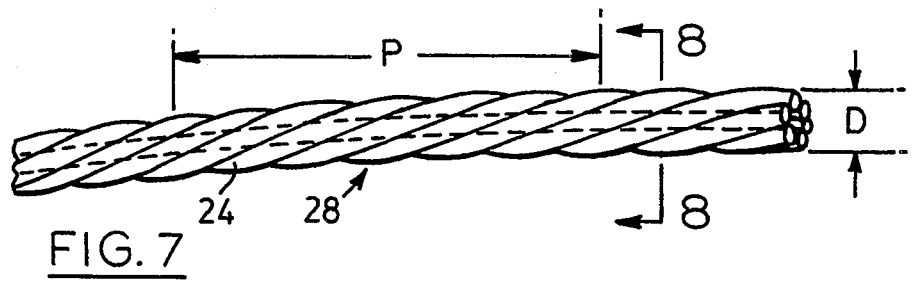
FIG. 7 is a side elevation of a wrapped coreless multi-strand arch wire which is another embodiment of the invention.

FIGS. 7 and 8 are respectively a side elevation and a transverse cross section of another arch wire of the invention, this wire also comprising a plurality of wrapping strands 24 (six in this embodiment) of a superelastic metal alloy, such as a nickel/titanium alloy, wrapped helically parallel to one another. However, with this embodiment, although the wire will usually be manufactured using a central core strand 26 as a winding mandrel, and as a mandrel during the formation of the arch wires, the core strand is removed before delivery to the orthodontist of the final product, whether a coil of the wire or individual arch wires, so that the wire has a central cylindrical hollow space 27 in place of the core strand. The removed core wire strand can also be of diameter from 0.127 mm (0.005 in) to 0.304 mm (0.012 in) with a preferred value of 0.178 mm (0.007 in), this value of course setting the diameter of the space 27 which it leaves, and also of the wrapping strands to obtain the desired final external diameter. It is preferred for economy in manufacturing these arch wires to adjust the overall diameter D of the wire primarily by adoption of a core strand of appropriate diameter, so that wrapping strands of the same diameter can be used for the different size wires. FIG. 8 shows the wire in its neutral wrapped configuration, in which the central space 27 is of exactly the same diameter as the core wire which it replaces. These coreless wires are also wound to have a P/D ratio of between six and twelve.

It is found possible to use the arch wires of the invention also as either an inherent compression spring, or as inherent compression spring portions, or as an inherent traction spring, or as inherent traction spring portions, so that separate compression or traction springs are not required, as will be explained below. If separate springs are used then the wires are used with conventional relationships between the diameter of the wire and the dimensions of the bracket slots in which it is engaged.

Figure 9:
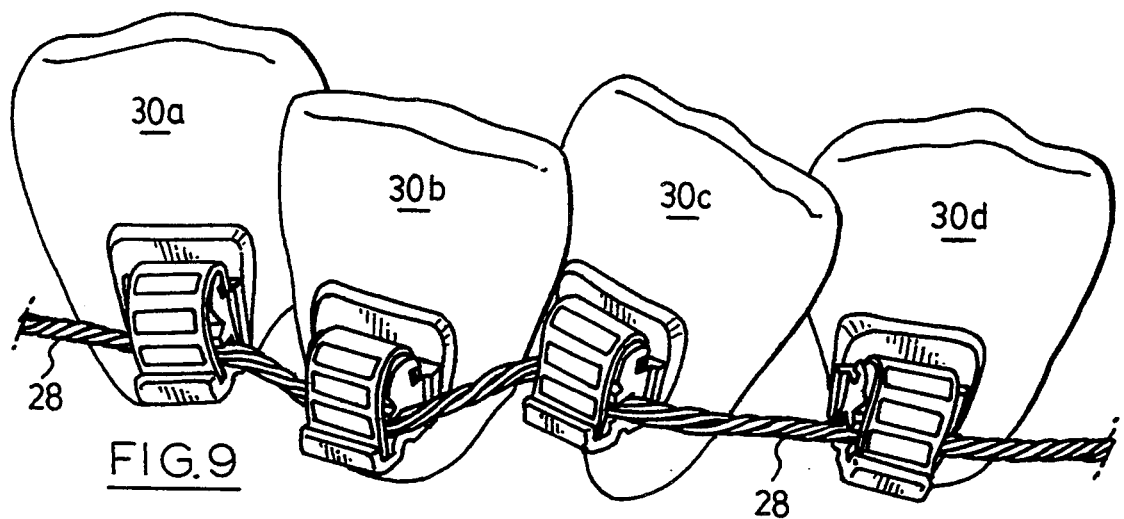
FIG. 9 is a perspective view from the labial and gingival of a plurality of malaligned teeth, each having a bracket attached thereto, and demonstrating the use of a coreless arch wire of the invention as a compression spring.
Figure 10:
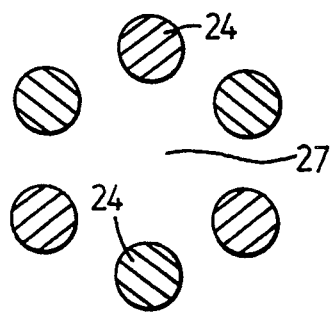
FIG. 10 is another transverse cross section through the wire of FIGS. 7, 8 and 9, showing a configuration of the strands with the wire acting as a compression spring.

FIG. 9 illustrates the manner in which a coreless arch wire 28 of FIGS. 7 and 8 can be used in an orthodontic procedure, and can also unexpectedly be made to operate as an inherent compression spring. A plurality of malaligned teeth 30a, 30b, 30c and 30d are each provided with a self-ligating bracket 18 and are connected by the arch wire 28; the Figure illustrates a clinical situation actually encountered in practice, and shows the extreme deflection that is possible with the arch wires of the invention without the dangers of permanent set by overstressing and breakage of the wire. The Figure also illustrates the manner in which the wire is also able to function when required as a compression spring, and particularly as specifically located compression spring elements, without the need for separate springs mounted on the wire or connected between the operative orthodontic elements. For this purpose the wire is slightly oversize in diameter for the bracket slots, so that it must be squeezed into each slot and will distort slightly from its truly round cross section shape. For example, with a bracket slot of the size given above {0.55 mm (0.022 in) gingival occlusal dimension and 0.71 mm (0.028 in) labial lingual dimension} the diameter D of the wire is increased from 0.51 mm (0.020 in) to 0.61 mm (0.024 in), while the central space 27 has a diameter of 0.20 mm (0.008 in). It will be seen that the two outer teeth 30a and 30d must be pushed apart to provide adequate room for the two inner teeth 30b and 30c as they are all rotated into alignment with one another. Accordingly, as the wire is engaged in the slots of the inner teeth brackets a slightly longer length of the wire is provided between the immediately adjacent brackets than would be the case with a prior art wire. This results in the portions of the strands between the brackets being spread radially apart from their neutral wrapped configuration (FIG. 8), to the spread configuration illustrated by FIG. 10. Each portion of the wire having its strands spread in this manner acts as an independent compression spring element under its urge to return to the neutral wrapped configuration. This spreading cannot of course take place where the wire is constrained by its engagement in the bracket slots or end retainer tubes. The fundamentally different mode of operation that is involved is exemplified by the fact that reduction of friction between the bracket and wire is no longer desired, and instead sufficient friction is deliberately produced to ensure that there can be no sliding movement along the wire and instead the bracket moves with the wire.

Figure 11:
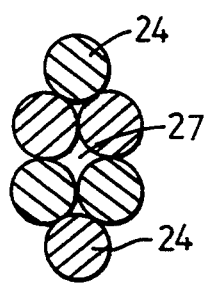
FIG. 11 is a further transverse cross section through the wire of FIGS. 7, 8 and 9, showing a configuration of the strands with the wire acting as a traction spring.

If instead the teeth are widely spaced and require to be drawn together the same oversize wire is used, but it is engaged in each pair of immediately adjacent bracket slots under sufficient tension that the strand portions of the respective portion of the wire between the brackets are closed radially inward from the neutral wrapped configuration of FIG. 8 to the closer configuration illustrated by FIG. 11, so that each wire portion acts as a corresponding traction spring portion by its urge to return to the neutral configuration.

Figure 12:
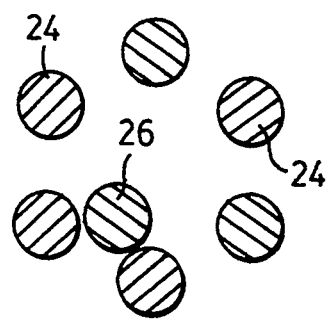
FIG. 12 is another transverse cross section through the wire of FIGS. 5 and 6, showing a configuration of the strands with the wire acting as a compression spring.

A cored wire as described and illustrated by FIGS. 5 and 6 can also be made to operate as a compression spring, or as compression spring elements, but less efficiently than a coreless wire, owing to the need for the core strand 26 to be displaced from its central position, and FIG. 12 illustrates what will usually happen to the individual strands when a cored wire is thus employed; it will be seen that the core strand 26 has moved off centre. The wire cannot however in practice be made to operate effectively as a traction spring, or as a traction spring element, owing to the presence of the central core strand blocking any inward movement of the wrapping strands.

Figure 13:
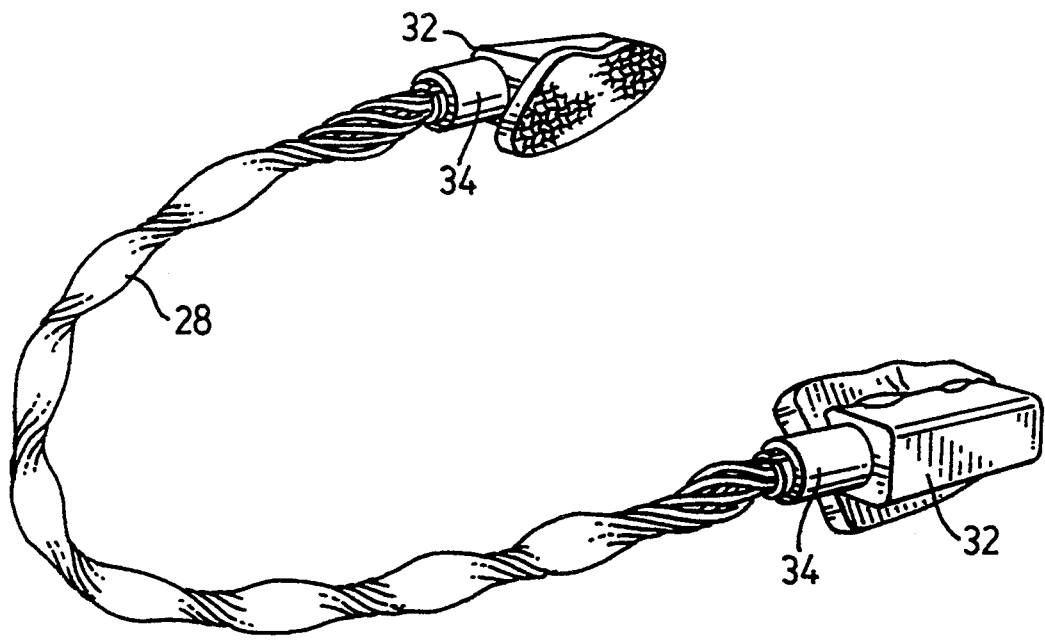
FIG. 13 is a perspective view of an arch wire of the invention, illustrating a manner in which the whole wire can be preset to operate as a compression spring.

FIG. 13 illustrates the manner in which the entire wire can be preset to operate as a compression spring or as separate compression spring segments. The two wire ends are, as usual, engaged in respective molar terminal tubes 32 cemented to their respective molars. The arch wire is cut to be slightly longer than is usually required (e.g. so that the anterior portion of the wire will rest 1-3 mm labial to the anterior brackets) and inserted in the terminal tubes. The wire is then forced into contact with the labial walls of the bracket slots and captured therein. When the wire has been engaged in all of the brackets the strands will spread radially outward, while also deflecting laterally, so that the wire portions between the brackets act as the respective compression spring segments or elements. Alternatively, as specifically illustrated, the wire can be cut to the usual length and the required protrusion of the anterior portion obtained by crimping end stops 34 on the wire ends that restrict their insertion into the terminal tubes by the desired amounts. If at some stage of the procedure it is decided that the wire is no longer needed to act as a compression spring, then all that is needed is to remove the end stops and allow the wire to enter fully into the terminal tubes.

Figure 14:
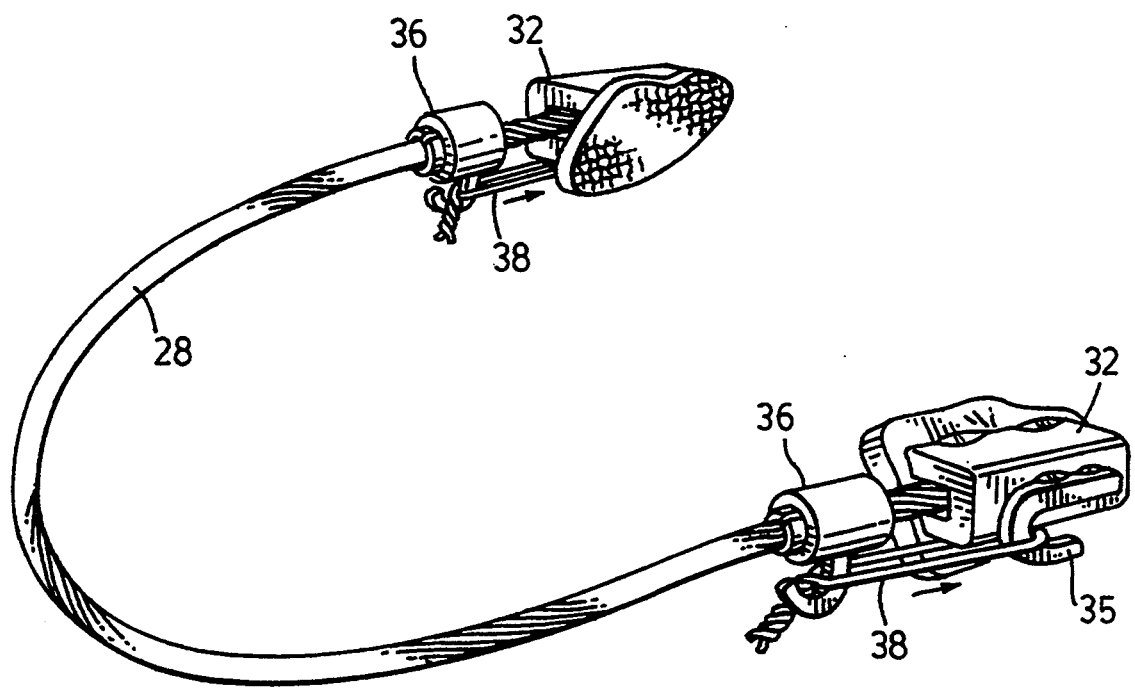
FIG. 14 is a perspective view of an arch wire of the invention, illustrating a manner in which the whole wire can be preset to operate as a traction spring.

FIG. 14 illustrates the manner in which the entire wire can be preset for its operation as a traction spring or as separate traction spring segments. The two wire ends are again engaged in respective molar terminal tubes 32 cemented to their respective molars, but these tubes are each provided with a respective ligature hook 35. The arch wire is cut to the usual size and arch wire gripping hooks 36 are attached to the wire about 1–3 mm mesial to the respective terminal tube. The gripping hooks are now drawn distally in the directions indicated by the arrows by ligature tie wires 38 attached between them and their respective molar tube hooks. The entire wire now has its strands strained radially inward, as illustrated by FIG. 11, so that the wire thins out and, as when the wire is acting as a compression spring, stores and subsequently releases this strain energy.

FIG. 15 is a typical stress strain characteristic for the superelastic recovery alloys, and it will be seen that, as compared for example to those for stainless steels, the typical hysteresis loop is wide and particularly flat, being very nearly parallel to the strain ordinate, and exhibiting what can be described as a nearly flat, long and level "loading superelastic plateau" and a nearly flat, long and level "unloading superelastic plateau". This particular loading plateau illustrates the desirable physical property of these metals which permits springs and wires made from them to be highly deflected without overstressing and permanent set. However, in the performance of this invention the long nearly flat unloading plateau is also of interest, and it is preferred that the critical unloading force be much lower than the critical loading force, with a plateau that is both low and as level as possible, corresponding to a restoring force that is low and as constant as possible over a very extended working range, so as to provide the desired behaviour for safe and rapid tooth displacement.

Figure 16A:
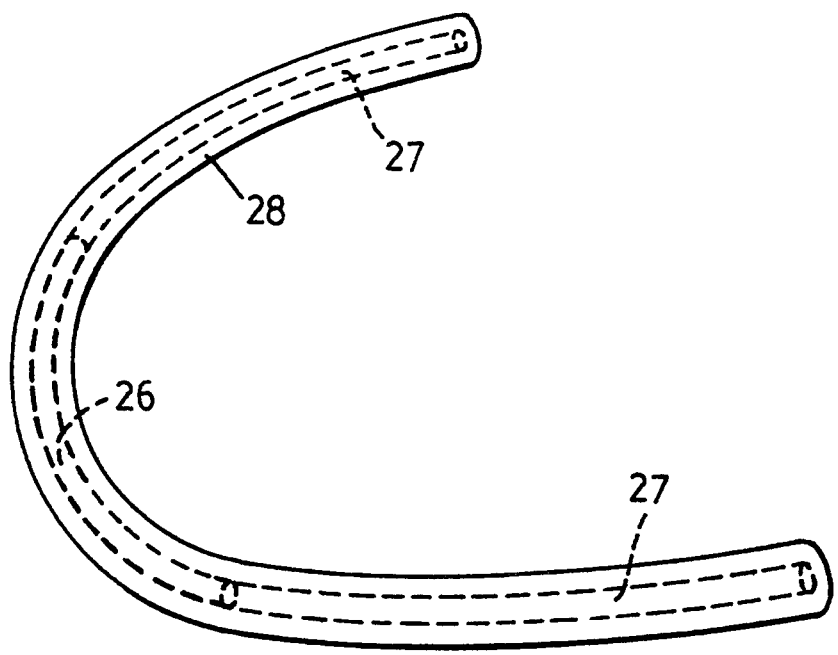
FIGS. 16a and 16b are side elevations of wrapped partial core arch wires of the invention, illustrating different possible dispositions for partial core portions.
Figure 16B:
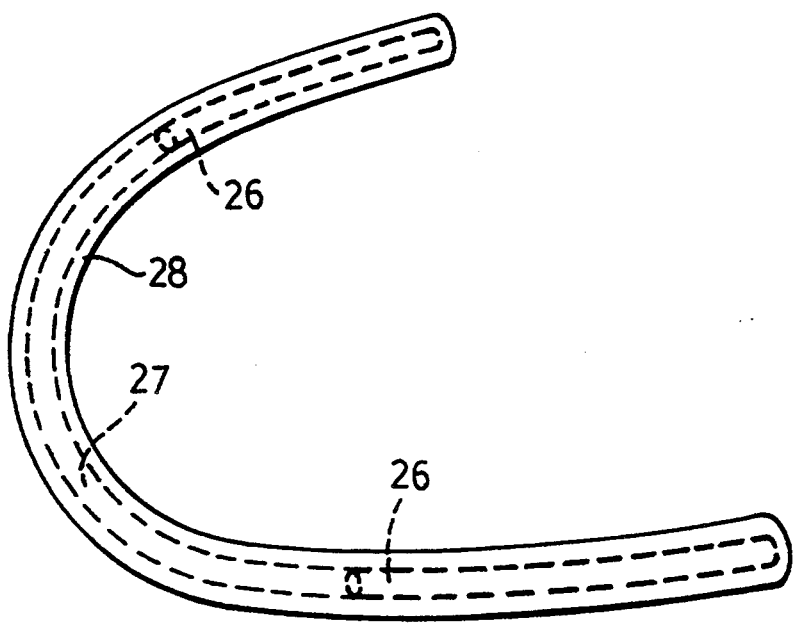

FIGS. 16a and 16b illustrate further embodiments of the invention in which the wire is provided with one or more partial core strand segments, the parts of the wire containing such a segment being inherently stiffer than the coreless portion. For example, as illustrated by FIG. 16a, the anterior portion of the arch wire that extends over the incisors is provided with a core segment 26, so that the wire is only able to permit very little compressive strain and virtually no traction strain in this location, the remaining side portions of the wire being coreless to permit these portions of the wire to be used for compression or traction as required. FIG. 16b illustrates the reverse situation in which the anterior portion of the arch wire is coreless so as to have a hollow 27, while the side portions of the wire that extend over the molars are provided with core portions 26. It is also possible to provide separate short core strand segments 26 in specific locations at which it is desired to provide a local restriction of the compression or traction strain.

Multistrand wires of higher values of the P/D ratio in the permitted range and with a large number of wrapping strands (e.g. eight and upwards) may have a problem in that they are likely to be more easily unravelled. The problem is not insurmountable and the ends can be cemented together or encased in a thin shrinkfit sleeve. A preferred solution is to use a crimpable end stop 40 as illustrated by FIGS. 17a, 17b and 17c, showing such a stop respectively ready for mounting on the end of a wire 28, mounted thereon, and crimped to attach it permanently to the wire. Such a stop is provided with core member 42 of the same diameter, or very slightly larger, than the arch wire central hollow 27, the core member being tapered towards its end to facilitate its insertion into the wire interior; the other end of the stop is rounded to prevent irritation of the adjacent mouth tissue. With the end stop in place the wire end protrudes into an annular recess 44 in which it is retained when the stop is crimped in place.

Although it is an advantage of the wires of the invention that they do not need to have their external surface smoothed to reduce or prevent the possibility of breakage, nevertheless such smoothing may be employed if the orthodontist prefers to operate with such a wire. A circular coreless cross section wire 28 is illustrated by FIG. 18 and preferably is formed by winding, usually on a central mandrel strand 27 that subsequently is removed, the required number of wrapping strands which are preformed with truncated segmental cross sections so that they fit snugly together in the final annular shape. Preferably a higher number, from eight to ten wrapping strands are used. A final low force rolling operation may be used to obtain the desired final exterior shape, but the force required will be much less than that needed if the wrapping strands must be deformed from their original circular cross sections.

Such a smoothing operation may also be employed, for example, to obtain a wire of other than approximately circular cross section to permit its use in a particular procedure. For example, in further embodiments the wire may be formed, e.g. by rolling, to have a square cross section as illustrated by FIG. 19, or a rectangular cross section, as illustrated by FIG. 20. The forming may take place about a round cross section core strand, as shown in solid line, or respectively about a preformed square or rectangular core strand, as illustrated in broken lines. If the wire is to be coreless then the core strand is removed at the end of the forming step, or subsequently just before the arch wire is formed therefrom.

FIG. 21 illustrates another possible transverse cross section for the wire, whether cored or coreless, which is usually referred to as a "speed" cross section in that it is particularly suitable for use in cooperation with my self-ligating brackets, its mode of operation being explained in detail in my U.S. Pat. No. 4,386,909, the disclosure of which is incorporated herein by this reference. FIGS. 22 and 23 illustrate further possible transverse cross sections for the wire, whether cored or coreless, usually referred to as being of D and extended D cross section, the mode of operation of these particular wires in cooperation with my self-ligating brackets being explained in detail in my U.S. Pat. No. 5,224,858, the disclosure of which is incorporated herein by this reference.

I claim:

1. An orthodontic arch wire for use in combination with a plurality of orthodontic elements attached to respective teeth in an orthodontic procedure;
   the arch wire comprising a plurality of wire strands of superelastic shape recovery metal alloy wrapped helically parallel to one another along the length of the wire;

wherein the ratio P/D of the longitudinal pitch P of the wire to the external diameter D of the wire is between six and twelve.

2. An arch wire as claimed in claim 1, wherein the wire is coreless so as to have a hollow cylindrical centre;

whereby at least a portion of the wire when frictionally engaged with two adjacent orthodontic elements with the strands of the portion spread radially apart from a neutral wrapped configuration acts between those two adjacent orthodontic elements as a compression spring by its urge to return to the neutral wrapped configuration.

3. An arch wire as claimed in claim 2, in combination with an end stop member at at least one end thereof, the end stop member having a core member that protrudes into the wire central hollow, and an annular recess into which the wire protrudes to permit the end member to be crimped on the wire end.

4. An arch wire as claimed in claim 1, wherein the wire is coreless so as to have a hollow cylindrical centre;

whereby at least a portion of the wire when frictionally engaged with two adjacent orthodontic elements with the strands of the portion closed radially inward from a neutral wrapped configuration acts between those two adjacent orthodontic elements as a traction spring by its urge to return to the neutral wrapped configuration.

5. An arch wire as claimed in claim 4, in combination with an end stop member at at least one end thereof, the end stop member having a core member that protrudes into the wire central hollow, and an annular recess into which the wire protrudes to permit the end member to be crimped on the wire end.

6. An arch wire as claimed in claim 1, wherein the material of the wire strands is selected from the group of superelastic shape recovery metal alloys consisting of nickel/titanium; nickel/titanium/copper; copper/zinc/aluminium; copper/zinc/aluminium/manganese; copper/aluminium/nickel; and copper/aluminium/nickel/manganese.

7. An arch wire as claimed in claim 1, wherein the material of the wire strands is nickel/titanium alloy of a nominal atomic composition of 50% nickel and 50% titanium, with small additions of copper, iron, cobalt or chromium.

8. An arch wire as claimed in claim 1, wherein the wire is provided along a part only of its length with a partial wire strand core.

9. An arch wire as claimed in claim 8, wherein the anterior portion of the wire for engagement with brackets on incisor teeth is provided with a partial wire strand core.

10. An arch wire as claimed in claim 8, wherein the posterior portions of the wire for engagement with brackets on molar teeth are provided with respective partial wire strand cores.

11. An arch wire as claimed in claim 1, in combination with molar end tubes into which its ends protrude, wherein the length of the wire is such that its anterior portion extends labially of the orthodontic brackets into which it is to be inserted so as to permit its functioning also as a compression spring.

12. An arch wire as claimed in claims 11, and comprising also stop members on the wire and butting the molar end tubes to limit the protrusion of the wire ends into the tubes.

13. An arch wire as claimed in claim 1, in combination with molar end tubes into which its ends protrude;

at least one of the molar end tubes having a respective anchor hook thereon;

at least one hook member attached to the wire spaced from the molar end tube having a hook thereon;

and a ligation member extending between the molar tube hook member and the hook member to apply traction to the wire so as to permit its functioning also as a traction spring.

14. An arch wire as claimed in claim 1, wherein the exterior of the wire is formed to a non-circular cross section.

15. An arch wire as claimed in claim 1, wherein the exterior of the wire is formed to a circular cross section, and the strands from which the wire is formed are preformed to be of truncated segmental cross section.

16. A new method of using an orthodontic arch wire in an orthodontic procedure;

wherein the arch wire comprises a plurality of wire strands of superelastic shape recovery metal alloy wrapped helically parallel to one another along the length of the wire, and the ratio P/D of the longitudinal pitch P of the wire to the external diameter D of the wire is between six and twelve;

comprising frictionally engaging at least a portion of the wire with two orthodontic members so that the strands of the portion between the two orthodontic members are spread radially apart from a neutral wrapped configuration, whereby the said portion of the wire acts as a compression spring by its urge to return to the neutral wrapped configuration.

17. A new method of using an orthodontic arch wire in an orthodontic procedure;

wherein the arch wire comprises a plurality of wire strands of superelastic shape recovery metal alloy wrapped helically parallel to one another along the length of the wire, and the ratio P/D of the longitudinal pitch P of the wire to the external diameter D of the wire is between six and twelve;

comprising frictionally engaging at least a portion of the wire with two orthodontic members so that the strands of the portion between the two orthodontic members are closed radially inward from a neutral wrapped configuration, whereby the said portion of the wire acts as a traction spring by its urge to return to the neutral wrapped configuration.

* * * * *